(12) United States Patent
Bonadio et al.

(10) Patent No.: US 6,796,940 B2
(45) Date of Patent: Sep. 28, 2004

(54) VISCERA RETAINER

(75) Inventors: Frank Bonadio, Bray (IE); Shane Joseph MacNally, Dublin (IE); Conor Hand, Balbriggan (IE); Alan Reid, Clontarf (IE)

(73) Assignee: Atropos Limited, County Wicklow (IE)

( * ) Notice: Subject to any disclaimer, the term of this patent is extended or adjusted under 35 U.S.C. 154(b) by 8 days.

(21) Appl. No.: 10/120,564

(22) Filed: Apr. 12, 2002

(65) Prior Publication Data

US 2003/0004473 A1 Jan. 2, 2003

Related U.S. Application Data

(63) Continuation of application No. PCT/IE00/00128, filed on Oct. 16, 2000.

(30) Foreign Application Priority Data

Oct. 14, 1999 (IE) .................................................. 990862

(51) Int. Cl.[7] .............................................. A61B 1/32
(52) U.S. Cl. ...................... 600/206; 600/208; 128/850
(58) Field of Search ............................... 600/207, 208, 600/206, 205, 231, 233, 235, 236; 128/850, 849; 602/42, 41, 43, 50, 60, 75, 63, 901, 6; 604/315, 358

(56) References Cited

U.S. PATENT DOCUMENTS

| 3,863,639 A | * | 2/1975 | Kleaveland | 128/850 |
| 4,848,364 A | * | 7/1989 | Bosman | 128/849 |
| 4,889,107 A | * | 12/1989 | Kaufman | 600/206 |
| 5,159,921 A | | 11/1992 | Hoover | |
| 5,231,974 A | | 8/1993 | Giglio et al. | |
| 5,879,290 A | * | 3/1999 | Bridges et al. | 600/206 |

FOREIGN PATENT DOCUMENTS

| EP | 0 267 640 | 5/1988 |
| WO | WO 99/47085 | 9/1999 |

* cited by examiner

Primary Examiner—Pedro Philogene
(74) Attorney, Agent, or Firm—Finnegan, Henderson, Farabow, Garrett & Dunner, LLP

(57) ABSTRACT

A retainer to retain the viscera displaced from an internal body area to be accessed for surgery comprises an outer envelope of pliable material with an evacuation port. At least two sheets of material are arranged in face to face relation in the envelope. The sheets have a forming configuration in which they are relatively free to slide over one another in conforming the envelope to a desired shape and a form retained configuration in which the sheets are restrained from sliding relative to one another on evacuation of the envelope. In one case there are sheets of an inelastic material and sheets of an elastic material. Alternatively the sheets may be of the same inelastic material.

17 Claims, 5 Drawing Sheets

VISCERA RETAINER

CROSS REFERENCE TO RELATED APPLICATIONS

This application is a continuation of International Application No. PCT/IE00/00128, filed Oct. 16, 2000, and claims priority of Irish Patent Application No. 990862, filed Oct. 14, 1999, the content of both of which is incorporated herein by reference.

INTRODUCTION

The invention relates to a viscera retainer for use in surgery.

Retraction of organs is necessary in surgery when the operative field would otherwise be obscured by the position of the organs. This happens for example in removal of the gall bladder when the liver must be retracted to allow the bladder to be identified, mobilised and removed or in surgery in the pelvic area when the small and large intestines must be retracted superiorly to permit access to the pelvic floor. Retraction can be achieved using surgical devices such as rigid retractors, soft surgical swabs, sponges or laparotomy packs.

Rigid retractors are usually flat metal or plastic devices that come in many shapes depending on the organ to be retracted. They are usually of a rounded, smooth construction in an attempt to be smooth against the wound edge or organ being retracted. A surgical department would have to have many of these different retractors for use in the different surgical procedures that were carried out in the hospital. These devices would usually be sterilisable and reusable. Rigid retractors are held in position either manually or by fixation to an external frame.

Swabs, sponges and laparotomy packs are gauze or other textile material folded several times into a square pack that may be rolled up or otherwise squashed into position in the abdomen to compress and displace internal organs away from the operative field. They are generally inconvenient to use.

EP-A-0267640 describes a form retainable unit comprising an airtight outer envelope, layers of flexible fibre material in the envelope and spheres between the layers of fiber material. On evacuation of the envelope the spheres become fixed in place and hold the envelope in a deformed holding configuration.

This form retainable unit works well in practice, however there are problems in manufacturing the required structure. Consequently, the costs of the manufactured unit are relatively high.

This invention is therefore directed towards providing an improved form retainable unit which will overcome at least some of these difficulties.

STATEMENTS OF INVENTION

According to the invention there is provided a viscera retainer for use in surgery comprising an outer envelope of pliable material, the envelope having an evacuation port, and at least two sheets of material arranged in face to face relation in the envelope, the retainer having a malleable forming configuration in which the sheets are relatively free to slide over one another in manipulating the retainer to a desired shape, and a form retained configuration in which the sheets are restrained from sliding relative to one another on evacuation of the envelope to retain the viscera displaced from an internal body area to be accessed for surgery.

In one embodiment of the invention the sheets are of the same material. In this case, preferably the sheets are of an inelastic material.

In another embodiment of the invention the sheets are of different materials. In this case one of the sheets is of less elastic material than the other sheet.

In a preferred embodiment the sheet of elastic material is of a deformable open-cell structure.

Preferably the sheet of elastic material is of a foam material. The foam may be a polyurethane foam.

Preferably the sheet of inelastic material is of closed cell construction. The sheet of inelastic material may be of polystyrene.

In one case the unit includes at least three sheets of material in the envelope.

In one case a pair of sheets of less elastic material sandwich a sheet of elastic material therebetween.

In another case a pair of sheets of elastic material sandwich a sheet of less elastic material therebetween.

In one embodiment of the invention the retainer includes mounting means for mounting the retainer in or adjacent an incision.

Preferably the mounting means comprises a mounting ring to which the retainer is attached.

In a preferred embodiment the mounting means has engagement means for engaging with a surgical device. In one case the surgical device is a wound retractor.

BRIEF DESCRIPTION OF DRAWINGS

The invention will be more clearly understood from the following description thereof given by way of example only with reference to the accompanying drawings, in which.

DETAILED DESCRIPTION

Figure 1:
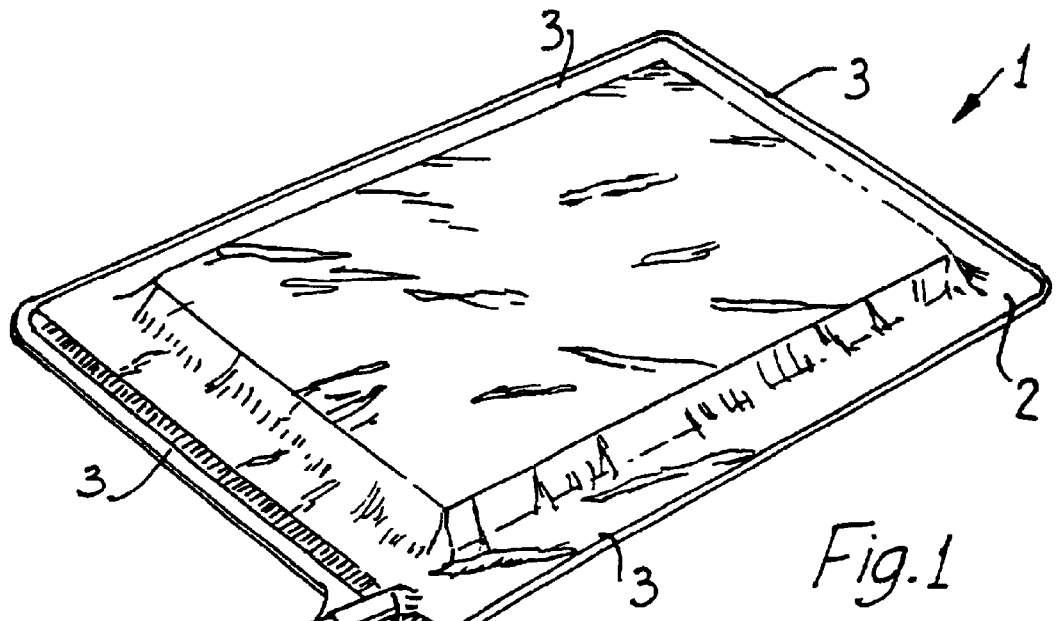
FIG. 1 is a perspective view of a viscera retainer unit according to the invention.
Figure 2:
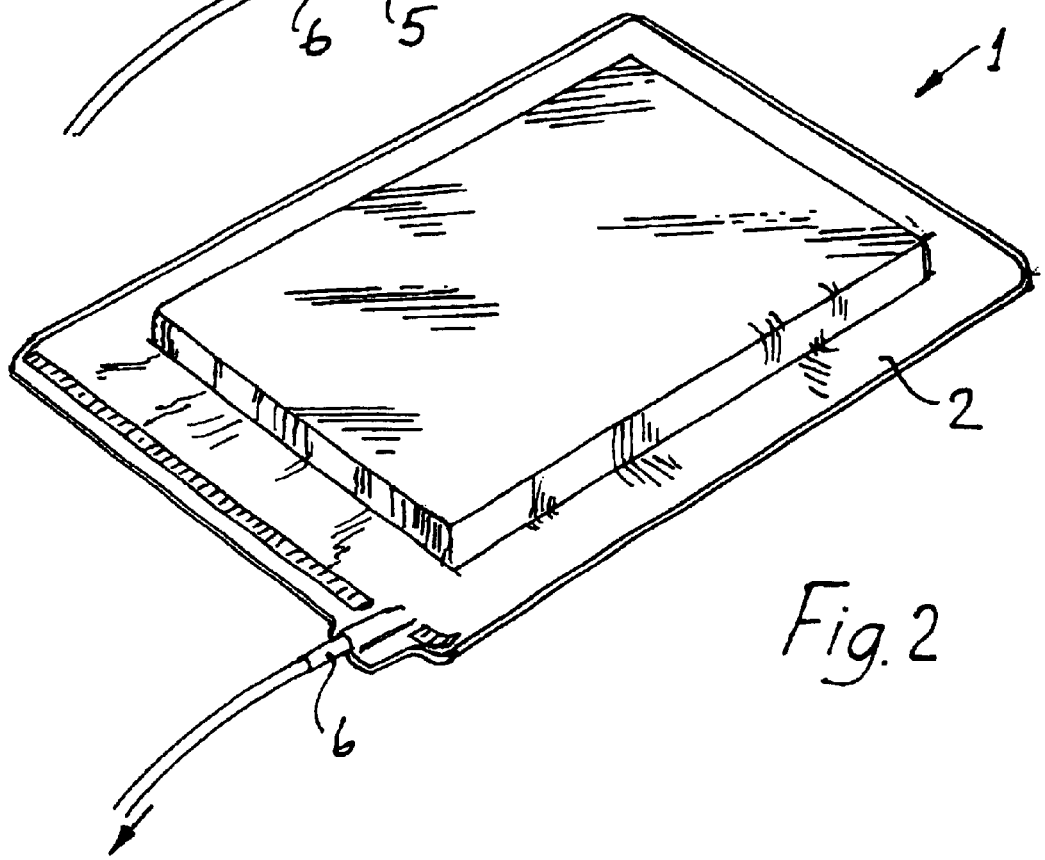
FIG. 2 is a perspective view of the retainer of FIG. 1 with a vacuum applied.

Referring to the drawings and initially to FIGS. 1 to 7 there is illustrated a viscera retainer 1 comprising an outer envelope 2 of substantially air-tight pliable plastics material formed by heat sealing a pair of sheets of plastics along side marginal edges thereof as indicated by heat welding lines 3. The envelope has an evacuation port 5 fitted with a tube 6 having a clamp (not shown). Air is drawn from the envelope 2 through the tube 6 and the tube 6 is closed by the clamp.

Figure 3:
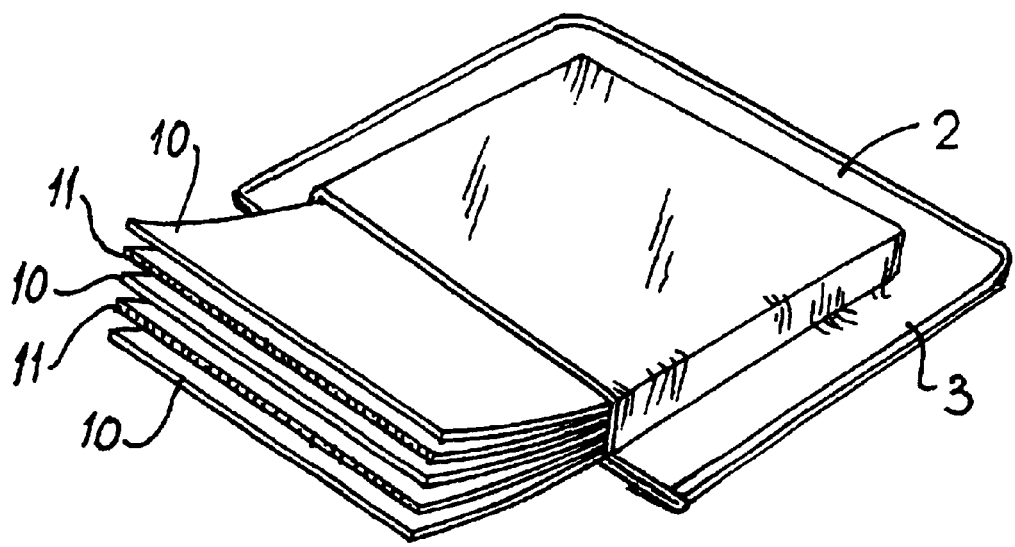
FIG. 3 is a diagrammatic cut-away and partially exploded view of the retainer of FIG. 2.

The envelope 2 has a sandwich structure comprising at least two and usually several sheets therein. In the arrangement of FIG. 3 there are alternate sheets of elastic material 10 and sheets of relatively inelastic material 11. In this case there are inner, outer and median sheets of elastic material sandwiching two sheets of relatively inelastic material. The envelope 2 is illustrated diagrammatically in FIG. 5. In use, it would be flush with the outer sheets.

The elastic sheets 10 are preferably of open cell foam material such as of a polyurethane foam. One such elastic material is available under the name Kayflex V60F from Advanced Materials Limited of Ireland.

The relatively inelastic sheets 11 are preferably of closed cell material such as of polystyrene material. One such relatively inelastic material is available under the name Epren from Advanced Materials Limited of Ireland.

The sheets 10, 11 are malleable and arranged in face to face relation in the envelope 2. During manipulation, the sheets 10, 11 are relatively free to slide over one another so that the envelope 2 and sheets 10, 11 can be conformed to a desired shape. The envelope 2 is then evacuated and the sheets 10, 11 are restrained from sliding relative to one another and the unit is thereby retained in a desired form retained configuration.

Figure 4:
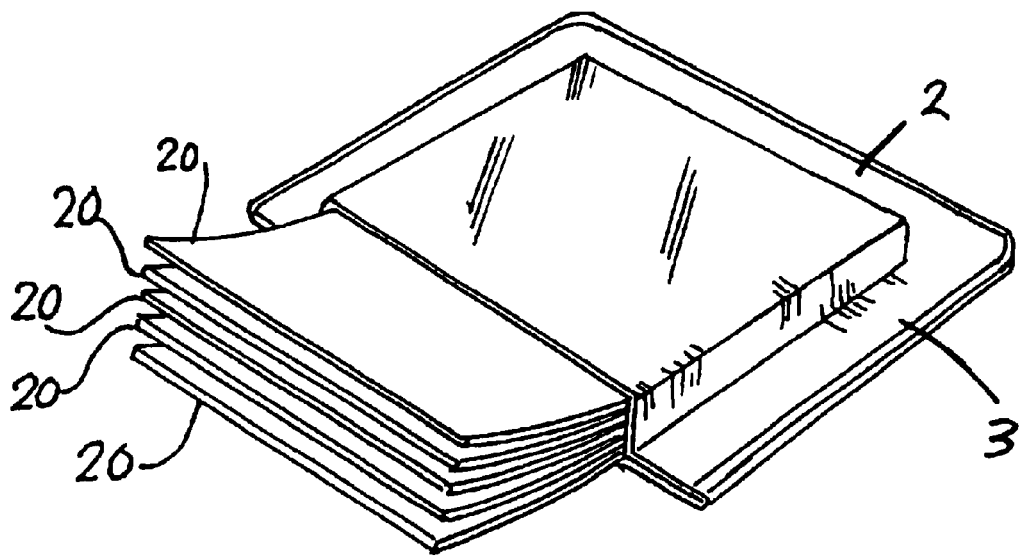
FIG. 4 is a diagrammatic cut-away view similar to FIG. 3 of another retainer unit of the invention.
Figure 5:
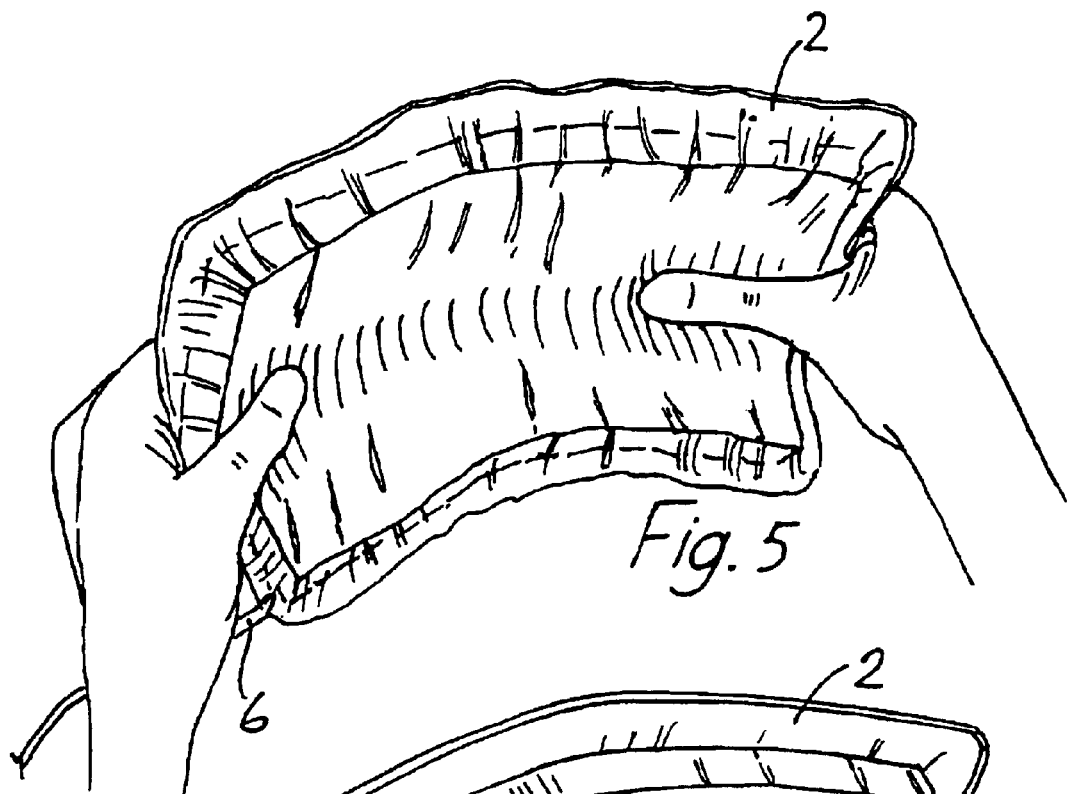
FIG. 5 is a perspective view of the retainer being formed into a desired configuration.
Figure 6:
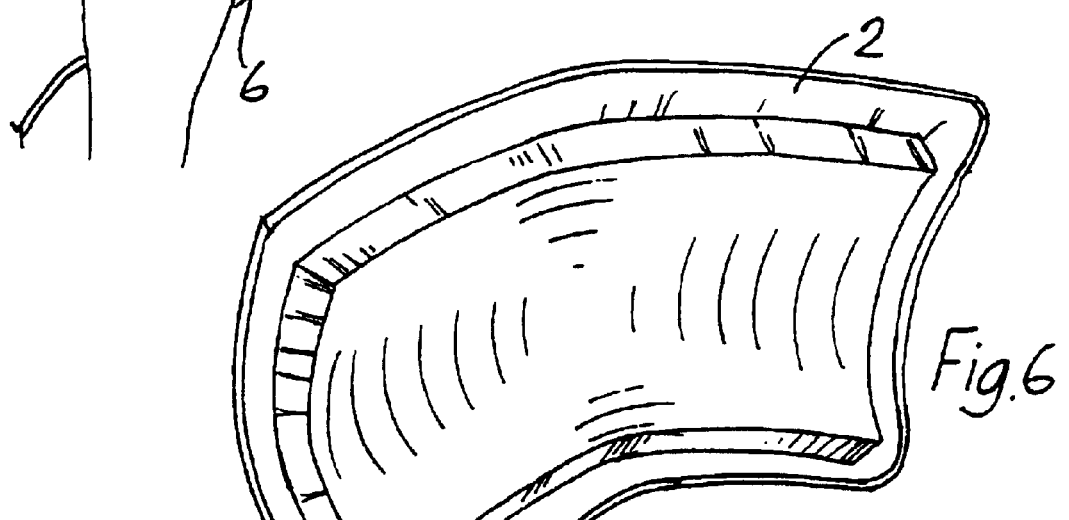
FIG. 6 is a perspective view of the retainer in a desired formed shape.
Figure 7:
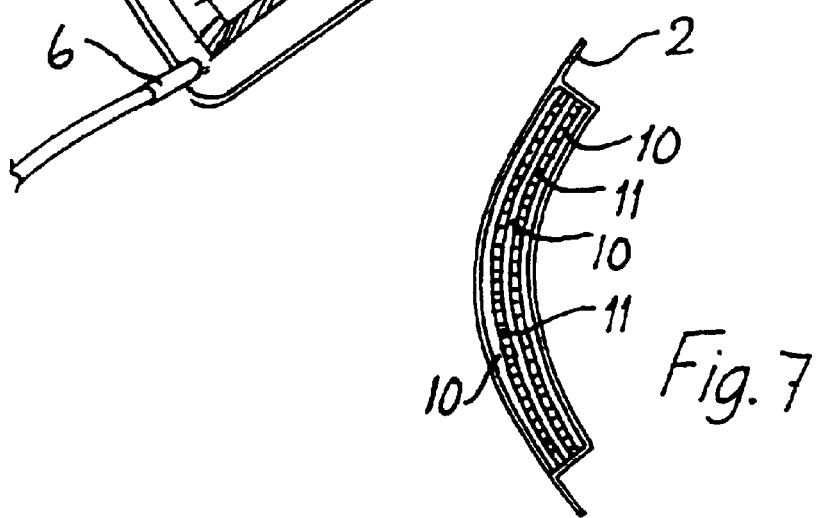
FIG. 7 is a transverse cross sectional view of the retainer in the configuration of FIG. 6.

In use, the viscera retainer is inserted into a wound opening and moulded into a required shape retaining, for example an organ in a desired position. The envelope 2 is then evacuated, the tube 6 is clamped and the unit retains the formed shape as illustrated in FIGS. 4 and 5 supporting and retaining an organ allowing a surgeon to continue an operation unimpeded. It will be apparent, particularly from FIG. 7 that the sheets slide relative to each other during forming and are maintained in a displaced configuration by the application of a vacuum.

In the arrangement of FIG. 4 all of the sheets 20 are of the same inelastic material such as that described above.

The malleable viscera retainer is used for retraction of internal organs during open surgery. Its function is to improve visibility in the area of interest during a surgical operation by compressing and displacing viscera such as abdominal organs, heart or lungs that would otherwise be in the way. This is generally referred to as surgical retraction.

The retainer is employed by positioning it within the abdominal cavity while it is in its relaxed, malleable state. When it is in the desired position a vacuum is applied causing the retainer to become rigid and maintain its shape and position. In this way the device acts as a surgical retractor. By releasing a clamp air is allowed to re-enter the envelope causing it to become malleable and formable again. In this way the retainer can be repositioned conveniently during surgery.

The retainer is soft and atraumatic. It is non-absorbent and its method of retraction is not dependent on staying dry.

Figure 8:
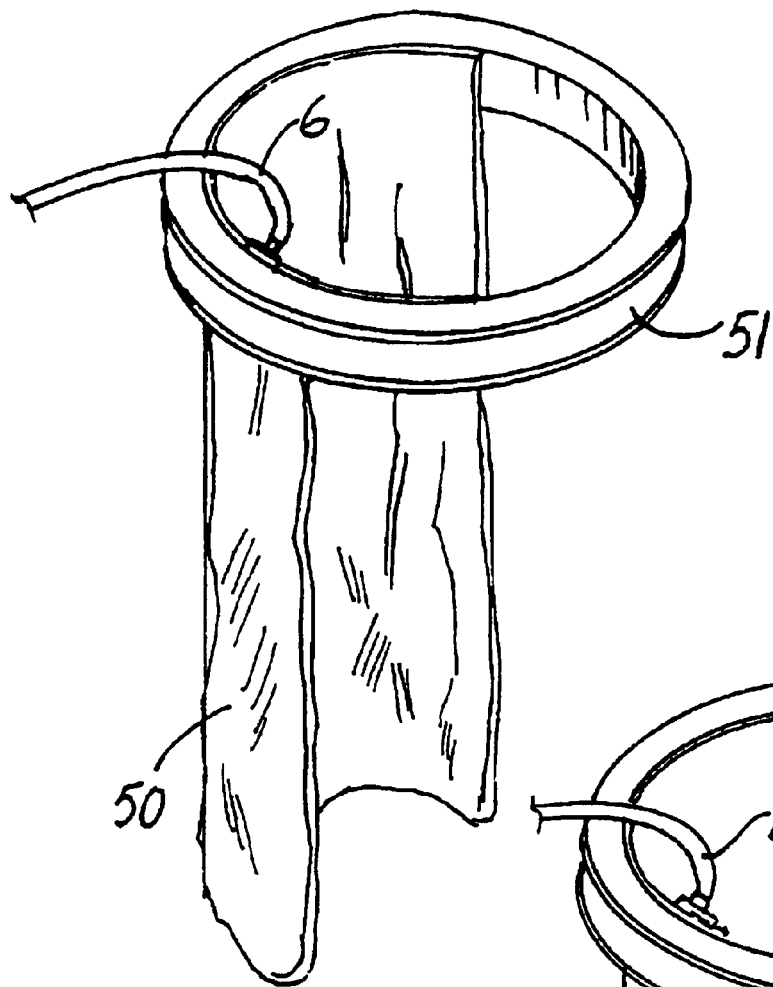
FIG. 8 is a perspective view of another viscera retainer of the invention.
Figure 9:
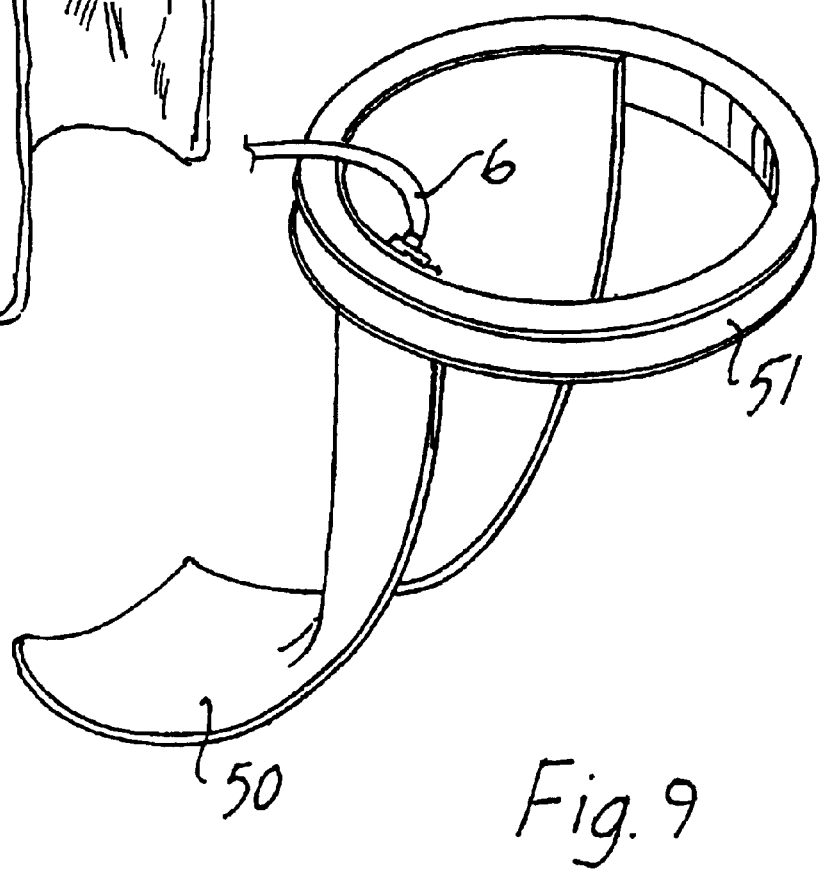
FIG. 9 is a perspective view of the retainer of FIG. 8 formed to a desired shape.
Figure 10:
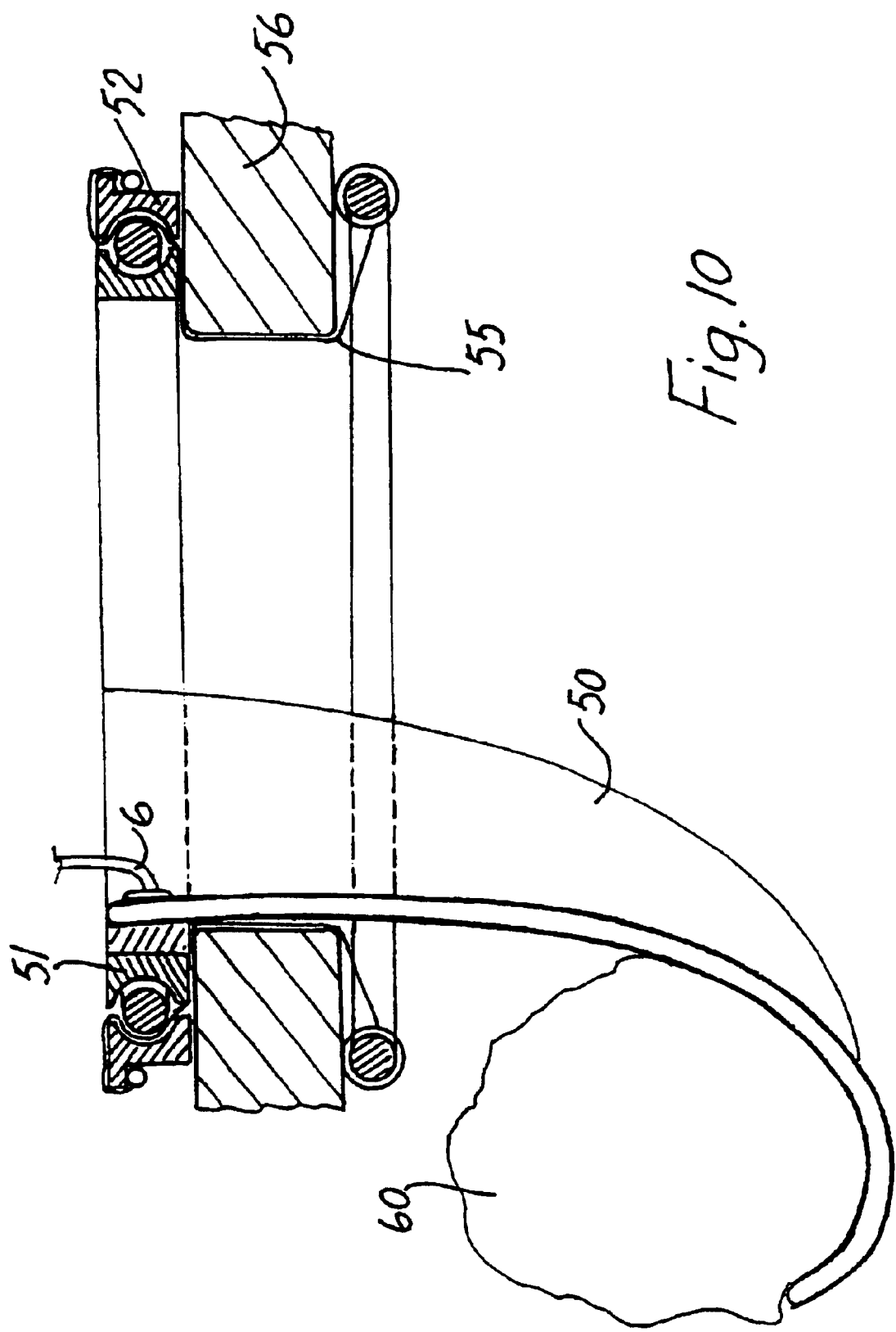
FIG. 10 is a cross sectional view of the retainer of FIGS. 8 and 9, in use.

Referring to FIGS. 8 to 10 there is illustrated another viscera retainer 50 according to the invention which is of the same envelope and sheet construction as described this case the retainer 50 in the unformed configuration is arcuate and is mounted to a mounting ring 51. The mounting ring 51 may, in turn be mounted to a wound protector retractor unit 52 in an incision 55, for example in the abdomen 56. The retainer 50 is used as described above, for example, to retain viscera such as an organ or part thereof indicated generally by the reference number 60 so that it does not obstruct access through the wound protector retractor unit 52.

The viscera retainer is inexpensive to manufacture as the sheets may be pre-cut to a desired size, are readily assembled in a sandwich configuration and housed within an envelope.

The invention is not limited to the embodiments hereinbefore described which may be varied in construction and detail.

What is claimed is:

1. A viscera retainer for use in surgery comprising an outer envelope of pliable material, the envelope having an evacuation port, and at least two sheets of material arranged in face to relation in the envelope, the retainer having a malleable forming configuration in which the sheets are relatively free to slide over one another in manipulating the retainer to a desired shape, and a form retained configuration in which the sheets are restrained from sliding relative to one another on evacuation of the envelope to retain the viscera displaced from an internal body area to be accessed for surgery.

2. A retainer as claimed in claim 1 wherein the sheets are of the same material.

3. A retainer as claimed in claim 2 wherein the sheets are of an inelastic material.

4. A retainer as claimed in claim 1 wherein the sheets are of different materials.

5. A retainer as claimed in claim 4 wherein one of the sheets is of less elastic material than the other sheet.

6. A retainer as claimed in claim 5 wherein the sheet of elastic material is of a deformable open-cell structure.

7. A retainer as claimed in claim 5 wherein the sheet of elastic material is of a foam material.

8. A retainer as claimed in claim 7 wherein the foam is a polyurethane foam.

9. A retainer as claimed in any of claim 3 wherein the sheet of inelastic material is of closed cell construction.

10. A retainer as claimed in any of claim 3 wherein the sheet of inelastic material is of polystyrene.

11. A retainer as claimed in claim 1 comprising at least three sheets of material in the envelope.

12. A retainer as claimed in claim 11 in which a pair of sheets of less elastic material sandwich a sheet of elastic material therebetween.

13. A retainer as claimed in claim 11 in which a pair of sheets of elastic material sandwiching a sheet of less elastic material therebetween.

14. A retainer as claimed in claim 1 including mounting means for mounting the retainer in or adjacent in incision.

15. A retainer as claimed in claim 14 wherein the mounting means comprises a mounting ring to which the retainer is attached.

16. A retainer as claimed in claim 14 wherein the mounting means has engagement means for engaging with a surgical device.

17. A retainer as claimed in claim 16 wherein the surgical device is a wound retractor.

* * * * *

UNITED STATES PATENT AND TRADEMARK OFFICE
CERTIFICATE OF CORRECTION

PATENT NO. : 6,796,940 B2
DATED : September 28, 2004
INVENTOR(S) : Frank Bonadio et al.

It is certified that error appears in the above-identified patent and that said Letters Patent is hereby corrected as shown below:

<u>Column 4,</u>
Lines 39 and 41, delete "any of" before "claim 13".

Signed and Sealed this

Seventh Day of December, 2004

JON W. DUDAS
*Director of the United States Patent and Trademark Office*